(12) United States Patent
Panandikar et al.

(10) Patent No.: US 9,492,459 B2
(45) Date of Patent: Nov. 15, 2016

(54) PHARMACEUTICAL COMPOSITION OF LINEZOLID

(71) Applicant: INDOCO REMEDIES LIMITED, Mumbai (IN)

(72) Inventors: Aditi Panandikar, Mumbai (IN); Sundeep Bambolkar, Mumbai (IN); Kavita Inamdar, Mumbai (IN); Sapna Ramesh, Mumbai (IN); Amol Burkul, Mumbai (IN); Nasir Shaikh, Mumbai (IN)

(73) Assignee: Indoco Remedies Limited, Mumbai (IN)

( * ) Notice: Subject to any disclaimer, the term of this patent is extended or adjusted under 35 U.S.C. 154(b) by 0 days.

(21) Appl. No.: 14/398,692

(22) PCT Filed: Aug. 2, 2013

(86) PCT No.: PCT/IN2013/000479
§ 371 (c)(1),
(2) Date: Nov. 3, 2014

(87) PCT Pub. No.: WO2014/033744
PCT Pub. Date: Mar. 6, 2014

(65) Prior Publication Data
US 2015/0093437 A1    Apr. 2, 2015

(30) Foreign Application Priority Data

Aug. 10, 2012 (IN) .................. 2290/MUM/2012

(51) Int. Cl.
*A61K 9/20* (2006.01)
*A61K 31/5377* (2006.01)
*A61K 47/36* (2006.01)

(52) U.S. Cl.
CPC .......... *A61K 31/5377* (2013.01); *A61K 9/205* (2013.01); *A61K 9/2095* (2013.01); *A61K 47/36* (2013.01)

(58) Field of Classification Search
CPC .................. A61K 31/5377; A61K 9/20
See application file for complete search history.

(56) References Cited

U.S. PATENT DOCUMENTS

| 4,251,518 A * | 2/1981 | Moore ............... A61K 9/205 514/54 |
| 6,514,529 B2 * | 2/2003 | Yamamoto ......... A61K 9/2054 424/464 |
| 7,714,128 B2 | 5/2010 | Rao et al. |
| 2006/0128703 A1 * | 6/2006 | Mohan Rao ......... C07D 263/20 514/235.2 |
| 2007/0104785 A1 * | 5/2007 | Navale .............. A61K 9/0007 424/466 |
| 2009/0068263 A1 * | 3/2009 | Antarkar ........... A61K 9/5078 424/470 |

FOREIGN PATENT DOCUMENTS

| WO | WO 2005035530 A1 * | 4/2005 |
| WO | 2007102082 A1 | 9/2007 |
| WO | 2010026597 | 3/2010 |
| WO | 2012029074 A2 | 3/2012 |

OTHER PUBLICATIONS

"International Search Report for PCT/IN2013/000479 dated Mar. 17, 2014".

* cited by examiner

*Primary Examiner* — Gollamudi Kishore
*Assistant Examiner* — Amanda Heyes
(74) *Attorney, Agent, or Firm* — Kramer Amado P.C.

(57) ABSTRACT

The present invention relates to a novel pharmaceutical composition of Linezolid. The present invention relates to a novel pharmaceutical composition comprising Linezolid Form III along with pharmaceutically acceptable excipients and a process to prepare the said composition. The present invention relates to an oral dosage forms for the treatment of severe infections caused by Gram-positive bacteria.

15 Claims, 3 Drawing Sheets

PHARMACEUTICAL COMPOSITION OF LINEZOLID

TECHNICAL FIELD

The present invention relates to a novel pharmaceutical composition of Linezolid. More particularly, the present invention relates to a novel pharmaceutical composition of Linezolid form III, Soy Polysaccharide as a disintegrant along with pharmaceutically acceptable excipients.

BACKGROUND & PRIOR ART

Linezolid is a synthetic antibiotic used for the treatment of serious infections caused by Gram-positive bacteria that are resistant to several other antibiotics. The empirical formula is $C_{16}H_{20}FN_3O_4$. Its molecular weight is 337.35, and its chemical structure is represented below:

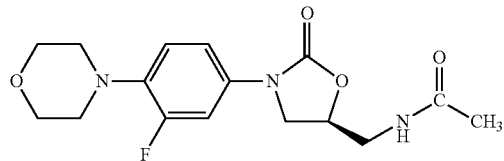 [SMILES: CC(=O)NC[C@H]1CN(c2ccc(N3CCOCC3)c(F)c2)C(=O)O1]

The main indication of Linezolid is the treatment of severe infections caused by Gram-positive bacteria that are resistant to other antibiotics; it should not be used against bacteria that are sensitive to drugs with a narrower spectrum of activity, such as penicillins and cephalosporins. In both, the popular press and the scientific literature, Linezolid has been called a "reserve antibiotic"one that should be used sparingly so that it will remain effective as a drug of last resort against potentially intractable infections.

Linezolid Form III, was discovered and described in U.S. Pat. No. 7,714,128. The crystalline form III was characterized by an x-ray powder diffraction spectrum having peaks expressed as 2θ at about 7.6, 9.6, 13.6, 14.9, 18.2, 18.9, 21.2, 22.3, 25.6, 26.9, 27.9 and 29.9 degrees.

WO2012029074 discloses pharmaceutical composition of Linezolid Form III, polacrilin potassium as disintegrant and hydroxypropylmethyl cellulose as binder along with pharmaceutically acceptable ingredients, prepared by dry granulation, wherein the composition retains Linezolid in its original crystalline form.

US20070104785 discloses pharmaceutical dosage of Linezolid Form III, water-insoluble polymer or colloidal silicon dioxide or clay or carbon dioxide source as means to reduce the gelling tendency of Linezolid along with pharmaceutically acceptable excipeints. However, there still persists the problem of erratic dissolution of the Linezolid from the dosage form.

WO2010026597 discloses a multiparticulate composition comprising a core in the form of beadlet or pellet, manufacture by extrusion and spheronization method, the core comprises Linezolid form III, one or more binders, and one or more disintegrants. Both processes require either special material or equipment which are not desirable for commercial production.

WO2007102082 assigned to Glenmark Pharmaceuticals Ltd discloses compositions of Linezolid crystalline Form II containing lactose-based water soluble excipient.

Linezolid Form III exhibits a gelling tendency when it comes into contact with water, which eventually leads to erratic dissolution of the Linezolid from the dosage form. Hence, there is a need to develop solid dosage forms of Linezolid Form III, which provides consistent dissolution profile.

The inventors of the present invention have used Soy Polysaccharides which exhibits excellent disintegration and improved dissolution characteristics of Linezolid Form III i.e. significantly reduces gelling tendency of Linezolid Form III. Its use in soluble systems has evidenced fast and efficient disintegration of oral dosage forms prepared with a varying range of hardness values.

Soy Polysaccharides is an all-natural, soft white to light-tan powder, which does not contain starch or sugar. It is derived from dehulled and defatted soybean flakes by a special process.

OBJECT OF THE INVENTION

An object of the present invention is to provide a novel pharmaceutical composition comprising Linezolid Form III, Soy Polysaccharide as disintegrant along with pharmaceutically acceptable excipients.

Another object of the present invention is to provide a novel pharmaceutical composition comprising Linezolid Form III, Soy Polysaccharide as disintegrant along with pharmaceutically acceptable excipients, wherein gelling tendency of Linezolid Form III is reduced and it retains its polymorphic form over the period of stability.

Another object of the present invention is to provide a novel pharmaceutical composition comprising Linezolid Form III, Soy Polysaccharide as disintegrant along with pharmaceutically acceptable excipients, which exhibits a complete and consistent dissolution profile.

Yet another object of the present invention is to provide a process for preparing a novel pharmaceutical composition comprising Linezolid Form III, Soy Polysaccharide as disintegrant along with pharmaceutically acceptable excipients.

Further object of the present invention is to provide a stable pharmaceutical composition comprising Linezolid Form III, Soy Polysaccharide as disintegrant along with pharmaceutically acceptable excipients.

Further object of the present invention is to provide a stable solid dosage form comprising Linezolid Form III, Soy Polysaccharide as a disintegrant to reduce gelling tendency of Linezolid Form III and one or more pharmaceutically acceptable excipients.

Still further object of the present invention is to provide a novel pharmaceutical composition for oral administration of Linezolid Form III for treating severe infections caused by Gram-positive bacteria.

SUMMARY OF THE INVENTION

The present invention provides a stable pharmaceutical composition comprising Linezolid Form III, Soy Polysaccharide as disintegrant along with pharmaceutically acceptable excipients and method of preparing the same, wherein the composition retains Linezolid in its crystalline Form III.

The present invention provides a method of preparing stable pharmaceutical composition comprising Linezolid Form III, Soy Polysaccharide as disintegrant along with pharmaceutically acceptable excipients.

DESCRIPTION OF THE INVENTION

The present invention provides a novel stable pharmaceutical composition comprising Linezolid Form III, Soy Polysaccharide as disintegrant along with pharmaceutically acceptable excipients.

In particular, the present invention provides a stable, immediate release solid oral pharmaceutical composition comprising Linezolid Form III, Soy Polysaccharide as disintegrant along with pharmaceutically acceptable excipients and a method of preparing the same.

In accordance with the present invention, methods of preparing pharmaceutical composition employed are wet granulation, dry granulation and direct compression, preferably dry granulation.

In one embodiment, method of preparing pharmaceutical composition is by dry granulation. Method of manufacturing by dry granulation includes mixing of Linezolid with one or more pharmaceutically acceptable excipients, further compaction followed by milling, sieving and addition of pharmaceutically acceptable excipients, lubrication, compression and coating.

In one embodiment, dry granulation can be performed by roller compaction. In one embodiment, dry granulation can be performed by slugging.

In one embodiment, the present invention involves dry granulating Linezolid Form III with Soy Polysaccharides as disintegrant, hydroxypropyl cellulose as a binder with one or more pharmaceutically acceptable excipients to develop a novel formulation without polymorphic form conversion.

In preferred embodiment, the present invention involves dry granulation of Linezolid Form III with Soy Polysaccharides as disintegrant with one or more pharmaceutically acceptable excipients to develop a stable formulation without polymorphic form conversion.

In one embodiment, the present invention is to provide a novel pharmaceutical composition comprising Linezolid Form III, Soy Polysaccharide as disintegrant, Hydroxypropyl cellulose as binder and optionally one or more additional excipients.

According to another embodiment, method of preparing pharmaceutical composition is by wet granulation. Method of manufacturing by wet granulation includes dry mixing of Linezolid Form III in a therapeutically effective amount with other pharmaceutically acceptable excipients, then granulation, drying, milling, addition of extra-granular excipients, lubrication, compression of the lubricated blend into tablets and coating of the compressed tablets.

In one embodiment, the present invention involves wet granulating Linezolid Form III using non aqueous solvents, Soy Polysaccharides as disintegrant, hydroxypropyl cellulose as binder and one or more pharmaceutically acceptable excipients to develop a novel formulation without polymorphic form conversion.

According to another embodiment, method of preparing pharmaceutical composition is by direct compression. Method of manufacturing by direct compression includes mixing of Linezolid Form III with pharmaceutically acceptable excipients, lubrication, compression and then coating.

In accordance with the present invention pharmaceutical composition comprises Linezolid and one or more diluents, binders, lubricants, glidants, disintegrants and coating agents.

The one or more diluents may be selected from mannitol, sorbitol, xylitol, lactose monohydrate, microcrystalline cellulose, light magnesium carbonate, dicalcium phosphate, tribasic calcium phosphate, calcium sulphate or mixtures thereof.

The one or more binders may be selected from hydroxypropyl methylcellulose, povidone (polyvinylpyrrolidone K-30), hydroxypropyl cellulose, maize starch or mixtures thereof.

The one or more lubricants may be selected from magnesium stearate, zinc stearate, calcium stearate, sodium stearyl fumarate, stearic acid or mixtures thereof.

Optionally colloidal anhydrous silica is used as glidant.

The one or more disintegrants may be selected from sodium starch glycolate, croscarmellose sodium, soy polysaccharide and cross-linked polyvinyl pyrrolidone, calcium carboxymethylcellulose or mixtures thereof. Preferred disintegrant used in the present invention is Soy Polysaccharide.

Opadry White is used as coating agent.

In accordance to the present invention, the pharmaceutical composition contains in parts by weight from about 60% to 90% Linezolid Form III, from about 1% to 20% diluent, from about 0.5% to 15% binder, from about 0.1% to 10% disintegrant, from about 1% to 3% lubricant.

In accordance with the present invention, Linezolid Form III is up to 90% by weight of solid dosage form.

In one embodiment, the pharmaceutical composition is in the form of solid oral dosage form.

In one embodiment, the pharmaceutical composition is in the form of tablet. The tablet is coated with coating agent. The coating is for aesthetic purpose and provides good appearance to the final dosage form.

In accordance with the present invention, the solid dosage form releases more than 90% of Linezolid in 45 minutes.

In accordance with the present invention, pharmaceutical composition manufactured with dry granulation process with compaction approach showed less gelling tendency in dissolution medium.

Although the invention has been described with reference to specific embodiments, this description is not meant to be construed in a limiting sense. Various modifications of the disclosed embodiments, as well as alternate embodiments of the invention, will become apparent to person skilled in the art upon reference to the description. It is therefore contemplated that such modifications can be made without departing from spirit or scope of the present invention as defined.

The invention is further exemplified with following examples and is not intended to limit the scope of the invention.

EXAMPLES

Example 1

| Example | mg | | | |
| --- | --- | --- | --- | --- |
|  | A | B | C | D |
| Intragranular | | | | |
| Linezolid | 600 | 600 | 600 | 600 |
| Maize starch | 40 | 40 | 20 | 20 |
| Microcrystalline cellulose | 44 | 44 | 113 | 113 |
| Soy Polysaccharide | 18.8 | — | — | — |
| Sodium starch glycolate | — | 12 | 12 | — |
| Croscarmellose sodium | — | — | — | 12 |
| Hydroxypropyl cellulose | 12 | 12 | 12 | 12 |
| Magnesium stearate | 4.2 | 4.2 | 4.2 | 4.2 |
| Extragranular | | | | |
| Microcrystalline cellulose | 76.8 | 93.6 | 44.60 | 44.60 |
| Soy Polysaccharide | 40 | — | — | — |
| Sodium starch glycolate | — | 30 | 30 | — |
| Croscarmellose sodium | — | — | — | 30 |

-continued

| Example | A | B | C | D |
|---|---|---|---|---|
| | | | mg | |
| Lubrication | | | | |
| Magnesium stearate | 4.2 | 4.2 | 4.2 | 4.2 |
| Theoretical weight of core tablets | 840 | 840 | 840 | 840 |
| Opadry white | 25.20 | 25.20 | 25.20 | 25.20 |
| Purified water | qs | qs | qs | qs |
| Theoretical weight of Coated tablets. | 865.20 | 865.20 | 865.20 | 865.20 |

Manufacturing Process
1. Linezolid was sifted through ASTM # 24 mesh.
2. Maize starch, Microcrystalline cellulose and disintegrant were sifted through ASTM # 40 mesh and dry mixed with step 1 for sufficient time.
3. Magnesium stearate was sifted through ASTM # 40 mesh and added into step 2 and was mixed for sufficient time.
4. The blend of step 3 was used to form compacts of sufficient hardness using Roller compactor.
5. The compacts of step 4 were milled using multi mill screen of 2 mm and were passed through ASTM #16 mesh.
6. Microcrystalline cellulose and disintegrant were sifted through ASTM # 40 mesh and loaded into blender of suitable size and were mixed with sized granules of step 5.
7. Magnesium stearate was sifted through ASTM # 40 mesh and added to step 6 and mixed for sufficient time.
8. Lubricated blend of step 7 was compressed into tablets.
9. Compressed tablets of step 7 were coated with Opadry white till weight gain of 3% was achieved.

Dissolution Data

| Time in minutes | Example 1A (40° C./75% RH Condition.) | | | |
|---|---|---|---|---|
| | Initial | 1 Month | 3 Months | 6 Months |
| 0 | 0 | 0 | 0 | 0 |
| 5 | 78 | 79 | 77 | 78 |
| 10 | 84 | 84 | 88 | 85 |
| 15 | 87 | 88 | 89 | 89 |
| 20 | 88 | 90 | 90 | 89 |
| 30 | 90 | 91 | 91 | 91 |
| 45 | 94 | 93 | 93 | 91 |

The dissolution was more than 90% in 45 minutes for the tablets of example 1A containing Soy Polysaccharide as disintegrant with reduced gelling tendency.

The crystallinity of polymorph is determined by using X-ray powder diffraction (XRD) at initial as well as stability stages.

DESCRIPTION OF DRAWINGS

Figure 1:
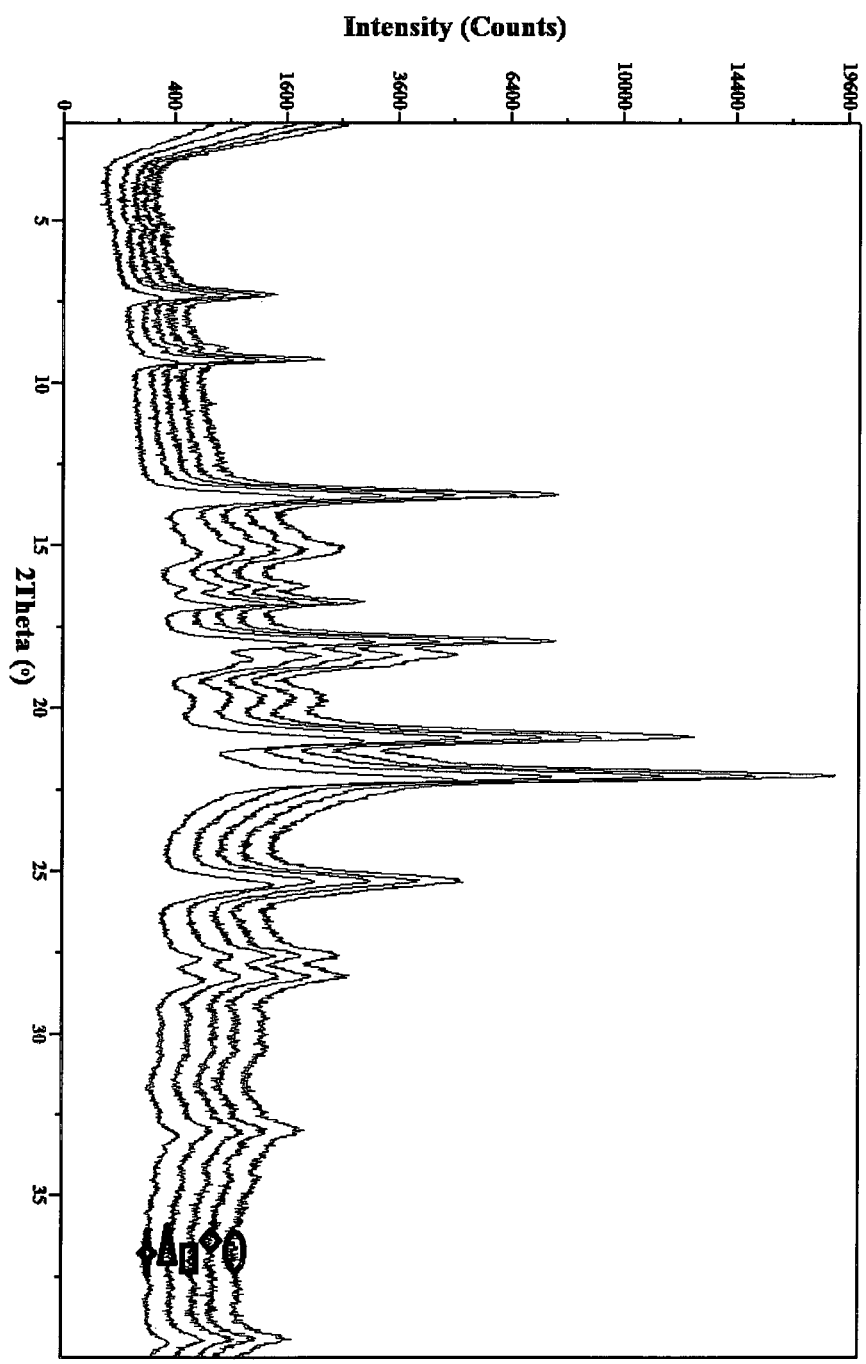
FIG. 1: Overlay XRD diffractograms of the Linezolid Form III pharmaceutical composition at 40° C./75 RH.

FIG. 1 depicts polymorphic content of pharmaceutical composition 1A which was determined by X-ray powder diffraction for Initial, 1, 2, 3 and 6 months respectively.

○—The symbol denotes XRD diffractogram for Initial period.
◆—The symbol denotes XRD diffractogram for 1 month.
□—The symbol denotes XRD diffractogram for 2 months.
◁—The symbol denotes XRD diffractogram for 3 months.
✦—The symbol denotes XRD diffractogram for 6 months.

Characteristic peaks at reflection angle 2θ (theta) values of Linezolid Form III viz. 7.038. 9.292, 13.439, 18.39, 18.657. 22.112 did not change for Initial, 1, 2, 3 and 6 months respectively.

Figure 2:
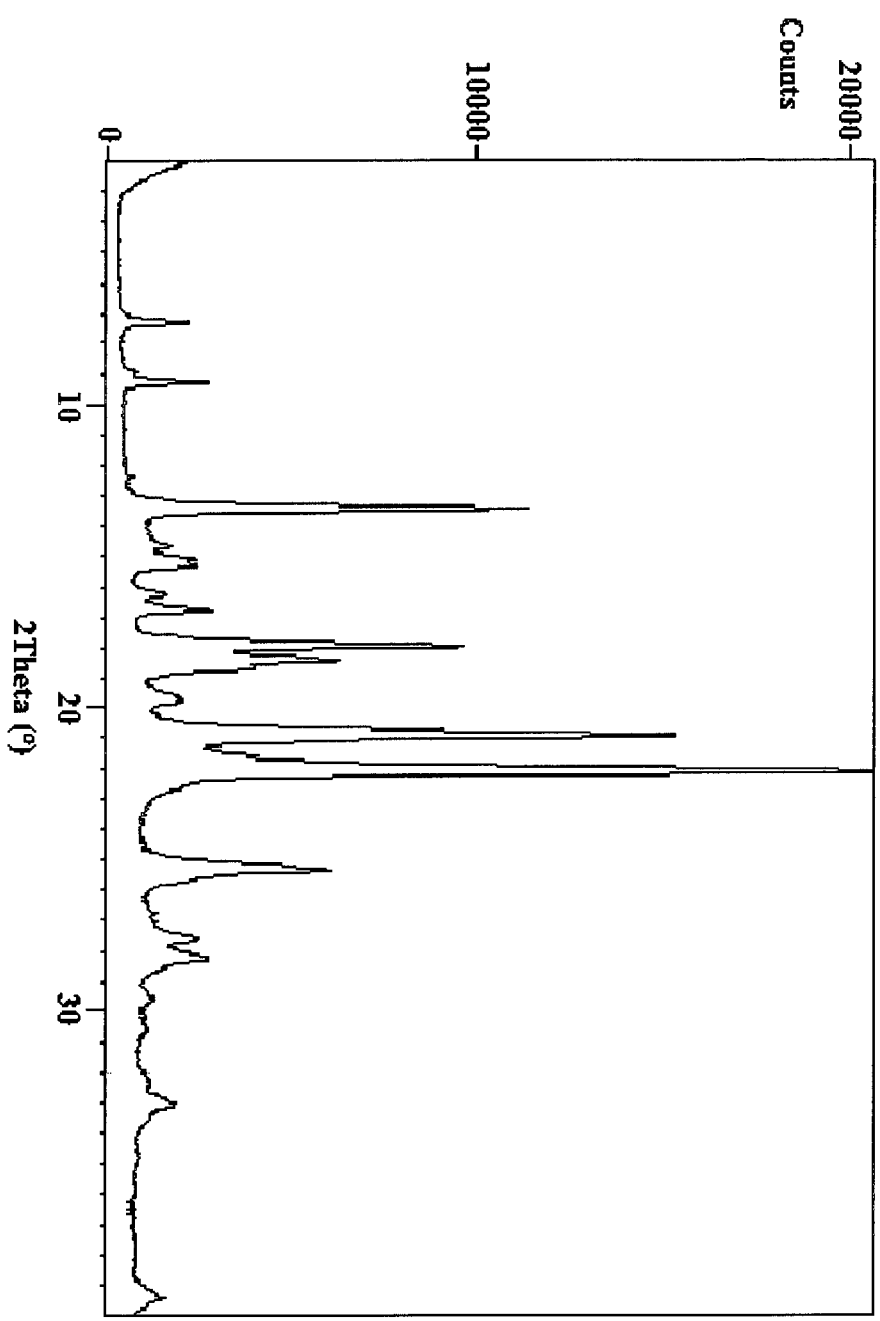
FIG. 2: XRD diffractogram of the Linezolid Form III.
Figure 3:
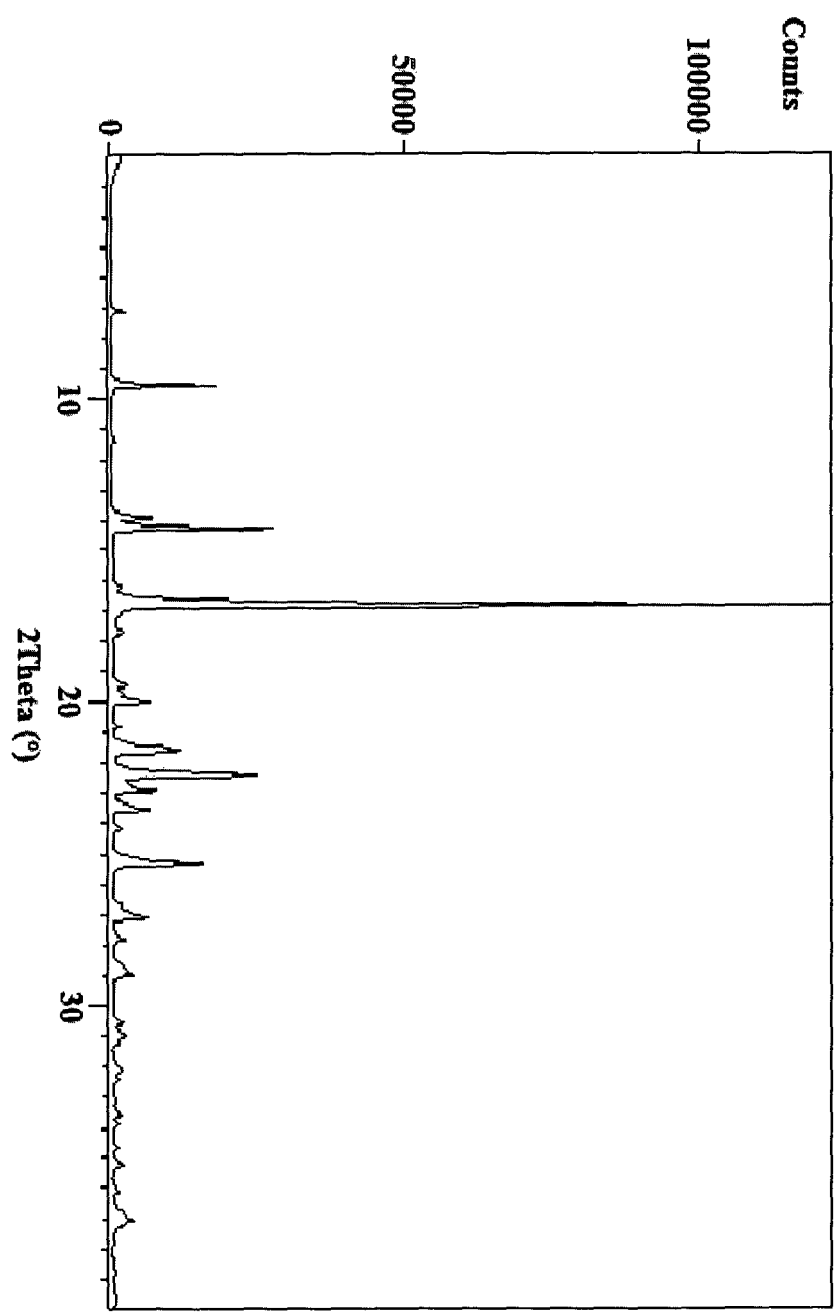
FIG. 3: XRD diffractogram of the Linezolid Form II.

FIG. 2 depicts Standard XRD diffractogram of Linezolid Form III.
FIG. 3 depicts Standard XRD diffractogram of the Linezolid Form II.

We claim:
1. A stable pharmaceutical composition consisting of:
   Linezolid Form III having an x-ray powder diffraction spectrum having peaks at about 7.6, 9.6, 13.6, 14.9, 18.2, 18.9, 21.2, 22.3, 25.6, 26.9, 27.9, and 29.9, expressed as degrees 2θ,
   soy polysaccharides as a disintegrant; and
   at least one of:
      a pharmaceutically acceptable non-polymeric excipient selected from the group consisting of mannitol, sorbitol, xylitol, lactose monohydrate, dicalcium phosphate, tribasic calcium phosphate, calcium sulphate, magnesium stearate, zinc stearate, calcium stearate, sodium stearyl furnarate, stearic acid, and mixtures thereof; and
      a polymer selected from the group consisting of microcrystalline cellulose, hydroxylpropyl methylcellulose, povidone, hydroxylpropyl cellulose, maize starch, and mixtures thereof;
   wherein said composition releases more than 90% of the Linezolid therein in 45 minutes upon contact with water.
2. The pharmaceutical composition of claim 1, wherein the pharmaceutical composition is a solid dosage form prepared by wet granulation.
3. The pharmaceutical composition of claim 1, wherein the composition releases more than 90% of the Linezolid therein in 45 minutes upon contact with water after storage for at least six months at 40° C. and 75% relative humidity.
4. The pharmaceutical composition as claimed in claim 1, consisting of Linezolid form III, Soy Polysaccharides, maize starch, microcrystalline cellulose, hydroxy propyl cellulose, and magnesium stearate.
5. A stable pharmaceutical composition consisting of:
   from 60% to 90% by weight of Linezolid Form III;
   from 0.1% to 10% by weight of soy polysaccharides as a disintegrant; and
   at least one pharmaceutically acceptable excipient selected from the group consisting of:
      a diluent selected from the group consisting of mannitol, sorbitol, xylitol, lactose monohydrate, microcrystalline cellulose, dicalcium phosphate, tribasic calcium phosphate, calcium sulphate, and mixtures thereof;
      a binder selected from the group consisting of hydroxylpropyl methylcellulose, povidone, hydroxylpropyl cellulose, maize starch, and mixtures thereof; and
      a lubricant;
   wherein the stable pharmaceutical composition does not contain colloidal silicon dioxide;

said Linezolid Form III having an x-ray powder diffraction spectrum having peaks at about 7.6, 9.6, 13.6, 14.9, 18.2, 18.9, 21.2, 22.3, 25.6, 26.9, 27.9, and 29.9, expressed as degrees 2θ.

6. The pharmaceutical composition of claim 5, wherein the x-ray powder diffraction spectrum of said Linezolid Form III is unchanged after storage for at least one month at 40° C. and 75% relative humidity.

7. The pharmaceutical composition of claim 5, wherein the x-ray powder diffraction spectrum of said Linezolid Form III is unchanged after storage for at least three months at 40° C. and 75% relative humidity.

8. The pharmaceutical composition of claim 5, wherein the x-ray powder diffraction spectrum of said Linezolid Form III is unchanged after storage for at least six months at 40° C. and 75% relative humidity.

9. A stable pharmaceutical composition consisting of:
Linezolid Form III;
soy polysaccharides as a disintegrant; and
at least one pharmaceutically acceptable excipient selected from the group consisting of:
  a diluent selected from the group consisting of mannitol, sorbitol, xylitol, lactose monohydrate, microcrystalline cellulose, dicalcium phosphate, tribasic calcium phosphate, calcium sulphate, and mixtures thereof;
  a binder selected from the group consisting of hydroxylpropyl methylcellulose, povidone, hydroxylpropyl cellulose, maize starch, and mixtures thereof; and
  a lubricant selected from the group consisting of magnesium stearate, zinc stearate, calcium stearate, sodium stearyl furnarate, stearic acid, and mixtures thereof;
said Linezolid Form III having an x-ray powder diffraction spectrum having peaks at about 7.6, 9.6, 13.6, 14.9, 18.2, 18.9, 21.2, 22.3, 25.6, 26.9, 27.9, and 29.9, expressed as degrees 2θ.

10. The pharmaceutical composition of claim 9, wherein the pharmaceutical composition is a solid dosage form.

11. The pharmaceutical composition of claim 10, wherein the solid dosage forms is a tablet.

12. The pharmaceutical composition of claim 11, wherein the tablet is prepared by direct compression.

13. The pharmaceutical composition of claim 12, wherein the tablet comprises up to 90% by weight of Linezolid Form III.

14. The pharmaceutical composition of claim 9, wherein the pharmaceutical composition is a solid dosage form prepared by dry granulation.

15. The pharmaceutical composition as claimed in claim 9, consisting of:
from 60% to 90% of said Linezolid form III, based on the weight of said tablet;
from 0.1% to 10% of said soy polysaccharides, based on the weight of said tablet;
from 1% to 20% of said diluent, based on the weight of said tablet, said diluent being microcrystalline cellulose;
from 0.5% to 15% of said binder, based on the weight of said tablet; and
from 1% to 3% of said lubricant, based on the weight of said tablet, said lubricant being magnesium stearate.

* * * * *